(12) United States Patent
Ichinose et al.

(10) Patent No.: US 11,468,659 B2
(45) Date of Patent: Oct. 11, 2022

(54) LEARNING SUPPORT DEVICE, LEARNING SUPPORT METHOD, LEARNING SUPPORT PROGRAM, REGION-OF-INTEREST DISCRIMINATION DEVICE, REGION-OF-INTEREST DISCRIMINATION METHOD, REGION-OF-INTEREST DISCRIMINATION PROGRAM, AND LEARNED MODEL

(71) Applicant: FUJIFILM Corporation, Tokyo (JP)

(72) Inventors: Akimichi Ichinose, Tokyo (JP); Keigo Nakamura, Tokyo (JP); Yoshiro Kitamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 93 days.

(21) Appl. No.: 17/000,363

(22) Filed: Aug. 23, 2020

(65) Prior Publication Data

US 2020/0387729 A1    Dec. 10, 2020

Related U.S. Application Data

(63) Continuation of application No. PCT/JP2019/004771, filed on Feb. 12, 2019.

(30) Foreign Application Priority Data

Mar. 16, 2018  (JP) .............................. JP2018-049799

(51) Int. Cl.
*G06V 10/20* (2022.01)
*G06K 9/62* (2022.01)
(Continued)

(52) U.S. Cl.
CPC ......... *G06V 10/255* (2022.01); *G06K 9/6256* (2013.01); *G06N 20/00* (2019.01); *G06T 7/0012* (2013.01); *G06T 2207/20081* (2013.01)

(58) Field of Classification Search
None
See application file for complete search history.

(56) References Cited

U.S. PATENT DOCUMENTS

2013/0006087 A1*  1/2013  Kondo .................. G16H 30/40
                                                          600/407
2016/0306936 A1  10/2016  Mizobe
(Continued)

FOREIGN PATENT DOCUMENTS

JP          2012198928          10/2012
JP          2016202904          12/2016
(Continued)

OTHER PUBLICATIONS

A. Garcia-Garcia et al., "A Review on Deep Learning Techniques Applied to Semantic Segmentation", Computer Vision and Pattern Recognition, Apr. 22, 2015, pp. 1-23.
(Continued)

*Primary Examiner* — Dov Popovici
(74) *Attorney, Agent, or Firm* — JCIPRNET

(57) ABSTRACT

A learning support device 18 includes an acquisition unit 26, a registration unit 27, a storage device 28, a learning unit 29, and a controller 31. The acquisition unit 26 acquires an image of a region of interest and a name of the region of interest by analyzing an interpretation report 23. The registration unit 27 registers training data consisting of the image of the region of interest and the name of the region of interest acquired by the acquisition unit 26 in the storage device 28. The learning unit 29 performs learning for generating a discrimination model 34, which outputs the image of the region of interest and the name of the region of interest with respect to an input of an inspection image 22 of the interpretation report 23, using a plurality of pieces of training data 33 registered in the storage device 28.

19 Claims, 10 Drawing Sheets

(51) Int. Cl.
    *G06N 20/00*     (2019.01)
    *G06T 7/00*     (2017.01)

(56) References Cited

U.S. PATENT DOCUMENTS

| | | | | |
|---|---|---|---|---|
| 2018/0150675 | A1* | 5/2018 | Kamiyama | G06V 20/693 |
| 2019/0027252 | A1* | 1/2019 | Calhoun | G06T 7/40 |
| 2019/0122397 | A1* | 4/2019 | Calhoun | A61B 6/488 |
| 2020/0035349 | A1 | 1/2020 | Mizobe | |

FOREIGN PATENT DOCUMENTS

| | | |
|---|---|---|
| WO | 2013001584 | 1/2013 |
| WO | 2017017722 | 2/2017 |

OTHER PUBLICATIONS

"International Search Report (Form PCT/ISA/210) of PCT/JP2019/004771," dated May 21, 2019, with English translation thereof, pp. 1-5.

"Written Opinion of the International Searching Authority (Form PCT/ISA/237) of PCT/JP2019/004771," dated May 21, 2019, with English translation thereof, pp. 1-10.

"Office Action of Japan Counterpart Application" with English translation thereof, dated Oct. 19, 2021, p. 1-p. 5.

\* cited by examiner

| INTERPRETATION REPORT |
| --- |
| PATIENT ID: 03355  INSPECTION ID: 0024 |
| INSPECTION DATE: 03/01/2018 |

FINDING

BOUNDARY-CLEAR PULMONARY NODULE HAVING $\phi$ = 30 mm IS RECOGNIZED IN RIGHT S1

ATTACHED IMAGE

LEARNING SUPPORT DEVICE, LEARNING SUPPORT METHOD, LEARNING SUPPORT PROGRAM, REGION-OF-INTEREST DISCRIMINATION DEVICE, REGION-OF-INTEREST DISCRIMINATION METHOD, REGION-OF-INTEREST DISCRIMINATION PROGRAM, AND LEARNED MODEL

CROSS-REFERENCE TO RELATED APPLICATIONS

This application is a Continuation of PCT International Application No. PCT/JP2019/004771 filed on Feb. 12, 2019, which claims priority under 35 U.S.C § 119(a) to Japanese Patent Application No. 2018-049799 filed on Mar. 16, 2018. Each of the above application(s) is hereby expressly incorporated by reference, in its entirety, into the present application.

BACKGROUND OF THE INVENTION

1. Field of the Invention

The present invention relates to a learning support device, a learning support method, a non-transitory computer readable recording medium storing a learning support program, a region-of-interest discrimination device, a region-of-interest discrimination method, a non-transitory computer readable recording medium storing a region-of-interest discrimination program, and a learned model.

2. Description of the Related Art

In a medical field, a region name is specified in an anatomical organ name, and a disease name is diagnosed. For example, in JP2016-202904A, a plurality of regions are specified for a three-dimensional image of a brain or the like (region segmentation). As the region segmentation, for example, as described in A Review on Deep Learning Techniques Applied to Semantic Segmentation, there is a case where semantic segmentation for ascertaining an image with a pixel level is used.

SUMMARY OF THE INVENTION

Names of regions of interest, such as an anatomical organ name, a segment name, a disease name, and a symptom, and images of the regions of interest are learned using machine learning, such as deep learning, and a name of a region of interest is determined from an image of the region of interest. In order to accurately determine the name of the region of interest, in deep learning, learning with massive and high-quality training data according to purposes is indispensable. Acquisition of training data from massive data, such as interpretation reports, stored in a medical information system, such as Picture Archiving and Communication System (PACS), has been examined. However, it is not reasonable to manually discriminate data useful for training data from massive data.

An object of the invention is to provide a learning support device, a learning support method, a non-transitory computer readable recording medium storing a learning support program, a region-of-interest discrimination device, a region-of-interest discrimination method, a non-transitory computer readable recording medium storing a region-of-interest discrimination program, and a learned model capable of massively and easily acquiring training data consisting of images of regions of interest and names of the regions of interest in a case where a discrimination model for determining a name or the like of a region of interest from an image of the region of interest is generated.

In order to achieve the above-described object, the invention provides a learning support device comprising a storage unit, an acquisition unit, a registration unit, and a learning unit. The storage unit stores an interpretation report including an image and text information. The acquisition unit acquires an image of a region of interest included in the image and a name of the region of interest included in the text information by analyzing the interpretation report. The registration unit registers training data consisting of the image of the region of interest and the name of the region of interest acquired by the acquisition unit. The learning unit performs learning for generating a discrimination model, which outputs the image of the region of interest and the name of the region of interest with respect to an input of the image of the interpretation report, using a plurality of pieces of the training data registered in the registration unit.

It is preferable that the acquisition unit acquires positional information of the region of interest by analyzing the interpretation report.

It is preferable that the interpretation report has link information for associating finding information included in the text information with the positional information of the region of interest included in the image, and the acquisition unit acquires the positional information of the region of interest from the link information.

It is preferable that the interpretation report has annotation information attached around the region of interest, and the acquisition unit acquires the positional information of the region of interest from the annotation information.

It is preferable that the acquisition unit acquires the image of the region of interest and the positional information of the region of interest by a region-of-interest discrimination unit that discriminates the region of interest from the image of the interpretation report.

It is preferable that, in a case where names of a plurality of regions of interest including a first name and a second name different from the first name are acquired by analyzing the interpretation report, the learning unit performs the learning using first training data including the first name as the name of the region of interest and second training data including the second name as the name of the region of interest.

It is preferable that, in a case where names of a plurality of regions of interest are acquired by analyzing the interpretation report, the learning unit performs learning using region position information relating to the positional information of the region of interest in addition to the training data.

It is preferable that the acquisition unit acquires, with reference to a hierarchical structure database that stores a name in a superordinate concept or a subordinate concept corresponding to a superordinate concept or a subordinate concept with respect to the name of the region of interest, the name in the superordinate concept or the subordinate concept from the name of the region of interest, and the learning unit performs the learning using training data consisting of the image of the region of interest and the name in the superordinate concept or the subordinate concept.

It is preferable that the acquisition unit decides, with reference to a similar name database that stores a plurality of similar names similar to one another in advance with respect to the name of the region of interest, a representative name from the plurality of similar names, and the learning unit performs the learning using training data consisting of the image of the region of interest and the representative name.

It is preferable that the acquisition unit newly acquires an image of the region of interest and a name of the region of interest in a case where the interpretation report is newly stored in the storage unit, the registration unit registers new training data consisting of the image of the region of interest and the name of the region of interest newly acquired by the acquisition unit, and the learning unit generates an updated discrimination model by performing learning again using a plurality of pieces of the training data including the new training data in a case where the new training data is registered.

It is preferable that, in a case where the newly stored interpretation report and a past interpretation report for the same patient are stored in the storage unit, the acquisition unit acquires an image of the region of interest included in an image of the past interpretation report by performing registration of the image of the past interpretation report, an image of the newly stored interpretation report, and the newly acquired image of the region of interest, the registration unit registers past image training data consisting of the image of the region of interest acquired based on the past interpretation report and the newly acquired name of the region of interest, and the learning unit generates the updated discrimination model by performing learning again using a plurality of pieces of the training data including the past image training data in a case where the past image training data is registered.

It is preferable that the interpretation report includes an electronic medical chart.

It is preferable that the acquisition unit acquires, as the name of the region of interest, an anatomical organ name, a segment name, a disease name, and a symptom. It is preferable that the segment name is, more specifically, segment name of a lung, a liver, and a brain.

The invention also provides a learning support method for a learning support device including a storage unit, an acquisition unit, a registration unit, and a learning unit. The learning support method comprises an acquisition step in which the acquisition unit acquires an image of a region of interest included in the image and a name of the region of interest included in the text information by analyzing the interpretation report, a registration step in which the registration unit registers training data consisting of the image of the region of interest and the name of the region of interest acquired by the acquisition unit, and a learning step in which the learning unit performs learning for generating a discrimination model, which outputs the image of the region of interest and the name of the region of interest with respect to an input of the image of the interpretation report, using a plurality of pieces of the training data.

The invention also provides a non-transitory computer readable recording medium storing a learning support program that causes a computer to function as a storage unit, an acquisition unit, a registration unit, and a learning unit. The invention also provides a learning support device that is a computer having a memory and a processor. The learning support device comprises a memory that stores an interpretation report including an image and text information, and a processor that acquires an image of a region of interest included in the image and a name of the region of interest included in the text information by analyzing the interpretation report, registers training data consisting of the acquired image of the region of interest and the acquired name of the region of interest, and performs learning for generating a discrimination model, which outputs the image of the region of interest and the name of the region of interest with respect to an input of the image of the interpretation report, using a plurality of pieces of the registered training data.

The invention also provides a region-of-interest discrimination device comprising a storage unit, an acquisition unit, a registration unit, a learning unit, and a discrimination unit. The discrimination unit discriminates the image of the region of interest and the name of the region of interest using the discrimination model in a case where the image of the interpretation report is input.

The invention also provides a region-of-interest discrimination method for a region-of-interest discrimination device including a storage unit, an acquisition unit, a registration unit, a learning unit, and a discrimination unit. The region-of-interest discrimination method comprises an acquisition step, a registration step, a learning step, and a discrimination step in which the discrimination unit discriminates the image of the region of interest and the name of the region of interest using the discrimination model in a case where the image of the interpretation report is input.

The invention also provides a non-transitory computer readable recording medium storing a region-of-interest discrimination program that causes a computer to function as a storage unit, an acquisition unit, a registration unit, a learning unit, and a discrimination unit that discriminates the image of the region of interest and the name of the region of interest using the discrimination model in a case where the image of the interpretation report is input.

The invention also provides a learned model that causes a computer to function as a storage unit, an acquisition unit, a registration unit, a learning unit, and a discrimination unit that discriminates the image of the region of interest and the name of the region of interest using the discrimination model in a case where the image of the interpretation report is input.

According to the invention, it is possible to provide a learning support device, a learning support method, and a learning support program for easily acquiring training data needed for learning in a medical field from an interpretation report and generating a discrimination model.

DESCRIPTION OF THE PREFERRED EMBODIMENTS

Figure 1:
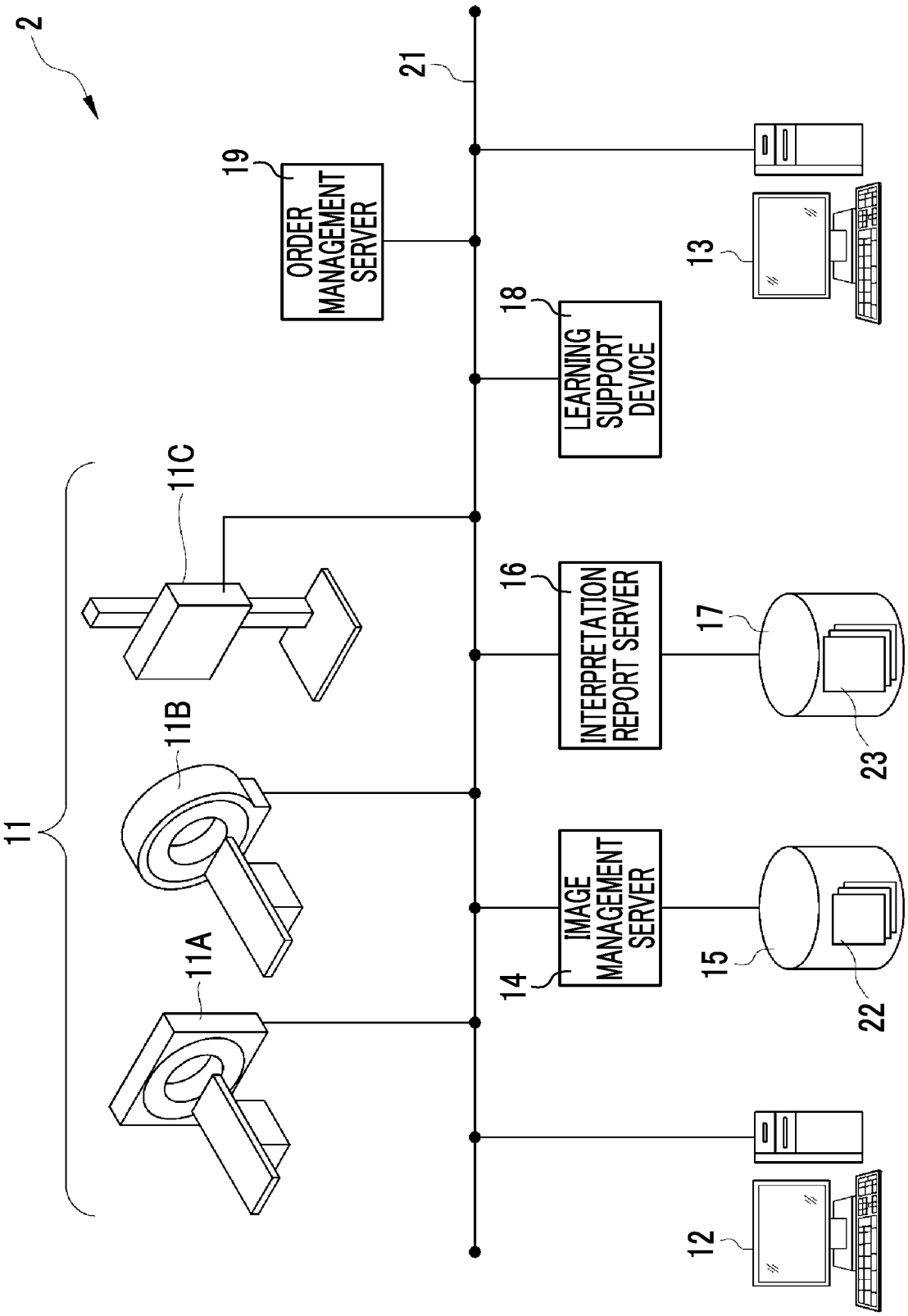
FIG. 1 is a diagram showing the schematic configuration of a medical information system.

In FIG. 1, a medical information system 2 has a modality 11, an interpretation doctor terminal 12, a treatment department doctor terminal 13, an image management server 14, an image database 15, an interpretation report server 16, an interpretation report database 17, a learning support device 18, and an order management server 19. The modality 11, the interpretation doctor terminal 12, the treatment department doctor terminal 13, the image management server 14, the image database 15, the interpretation report server 16, the interpretation report database 17, the learning support device 18, and the order management server 19 are connected to one another in a communicable state through a network 21, which is a local network, such as a local area network (LAN), provided in a medical facility. In a case where the interpretation doctor terminal 12 is provided in another hospital or a clinic, the local networks of the respective hospitals may be connected through the Internet or a dedicated line.

The medical information system 2 is a system that is provided for imaging of a part to be inspected of a subject and storage of a captured image, interpretation of the captured image and creation of an interpretation report of an interpretation doctor, and viewing of the interpretation report and detailed observation of the image of the target to be interpreted of a treatment department doctor as a client based on an inspection order from a treatment department doctor using a known ordering system.

In each equipment, an application program that causes the equipment to function as a component of the medical information system 2 is installed. The application program may be installed from a recording medium, such as a CD-ROM, or may be installed after downloaded from a storage device of a server connected by way of a network, such as the Internet.

The modality 11 includes an apparatus that images the part to be inspected of the subject to generate an inspection image 22 representing the part, attaches accessory information defined by a digital imaging and communication in medicine (DICOM) standard to the image, and outputs the image with the accessory information. The modality 11 also includes an apparatus that captures an image having three-dimensional information of an organ as an inspection image 22. As a specific example, a computed tomography (CT) apparatus 11A, a magnetic resonance imaging (MM) apparatus 11B, a positron emission tomography (PET) apparatus (not shown), an ultrasound apparatus (not shown), a computed radiography (CR) apparatus 11C using a flat panel detector (FPD), and the like are exemplified. In the following description, a lung is illustrated as an organ to be inspected for which the modality 11 performs imaging to generate an image.

The interpretation doctor terminal 12 is a computer that is used by an interpretation doctor in a radiology department for interpretation of an image or creation of an interpretation report, and comprises a known hardware configuration including a central processing unit (CPU), a main storage device, an auxiliary storage device, an input/output interface, a communication interface, an input device, a display device, a data bus, and the like. A known operating system and the like are installed in the interpretation doctor terminal 12. The interpretation doctor terminal 12 has one high-definition display or a plurality of high-definition displays as the display device. In the interpretation doctor terminal 12, processing, such as a transmission request of an image to the image management server 14, display of an image received from the image management server 14, automatic detection and highlighting a portion appearing to be a lesion in an image, and creation and display of an interpretation report 23, are executed by executing software programs for the respective processing. The interpretation doctor terminal 12 transfers the generated interpretation report 23 to the interpretation report server 16 through the network 21 and requests registration of the interpretation report in the interpretation report database 17.

The treatment department doctor terminal 13 is a computer that is used by a physician in a treatment department for detailed observation of an image, viewing of an interpretation report, viewing and input of an electronic medical chart, and the like, and comprises a known hardware configuration including a CPU, a main storage device, an auxiliary storage device, an input/output interface, a communication interface, an input device, a display device, a data bus, and the like. A known operating system and the like are installed in the treatment department doctor terminal 13. The treatment department doctor terminal 13 has one high-definition display or a plurality of high-definition displays as the display device. In the treatment department doctor terminal 13, processing, such as a viewing request of an image to the image management server 14, display of an image received from the image management server 14, automatic detection or highlighting of a portion appearing to be a lesion in an image, a viewing request of an interpretation report to the interpretation report server 16, and display of an interpretation report received from the interpretation report server 16, are executed by executing software programs for the respective processing.

In the image management server 14, a software program that provides a database management system (DBMS) function is incorporated into a general-purpose computer. The image management server 14 comprises a large-capacity storage for the image database 15. The storage may be a large-capacity hard disc device connected to the image management server 14 by a data bus or may be a disc device connected to a network attached storage (NAS) or a storage area network (SAN) connected to the network 21.

In the image database 15, inspection images (image data) 22 and accessory information obtained by imaging a plurality of patients with the modality 11 are registered. The accessory information includes, for example, information, such as an image identification (ID) for identifying an individual image, a patient ID for identifying a subject, an inspection ID for identifying an inspection, a unique identification (UID) allocated to each inspection image 22, inspection date on which the inspection image 22 is generated, an inspection time, the type of the modality 11 used in the inspection for acquiring the inspection image, patient information, such as a patient name, age, and sex, an inspection part (imaging part), imaging conditions (the presence or absence of use of a contrast medium, a radiation dose, and the like), and a series number in a case where a plurality of tomographic images are acquired by a single inspection.

In a case where a viewing request from the interpretation doctor terminal 12 is received by way of the network 21, the image management server 14 searches for an inspection image registered in the image database 15 and transmits the extracted inspection image to the interpretation doctor terminal 12 as a request source.

In the interpretation report server 16, a software program that provides a database management system (DBMS) function is incorporated into a general-purpose computer. In a case where a registration request of the interpretation report 23 from the interpretation doctor terminal 12 is received, the interpretation report server 16 registers the interpretation report 23 in the interpretation report database 17 in a format for a database.

In the interpretation report database 17, for example, the interpretation report 23, in which information, such as an image ID for identifying an image to be interpreted or a representative image, an interpretation doctor ID of an interpretation doctor who performs interpretation, a lesion name, positional information of a lesion, findings, and the certainty factor of findings, is recorded, is registered.

The order management server 19 receives an inspection order issued by the treatment department doctor terminal 13 and manages the received inspection order. The inspection order has, for example, various items, such as an order ID for identifying an individual inspection order, a terminal ID of the treatment department doctor terminal 13 that issues the inspection order or a treatment department doctor ID, a patient ID of a patient (hereinafter, referred to as a target patient) to be imaged according to the inspection order, an inspection purpose, such as follow-up observation, a part to be imaged, such as a head or a chest, and an orientation, such as supine or prone. An inspection technician in the radiology department confirms the contents of the inspection order by the order management server 19 and sets the imaging conditions according to the confirmed inspection order in the modality 11 to capture a medical image.

Next, a region-of-interest discrimination device 25 of the invention will be described referring to FIGS. 1 and 2. The region-of-interest discrimination device 25 is incorporated into, for example, the interpretation doctor terminal 12, and discriminate images of each segment of an organ and a portion appearing to be a lesion in the inspection image 22 and names of each segment of the organ and a region of interest. The interpretation doctor terminal 12 performs color-coding display of each segment of the organ, highlighting of the region of interest, or the like based on a discrimination result.

Figure 2:
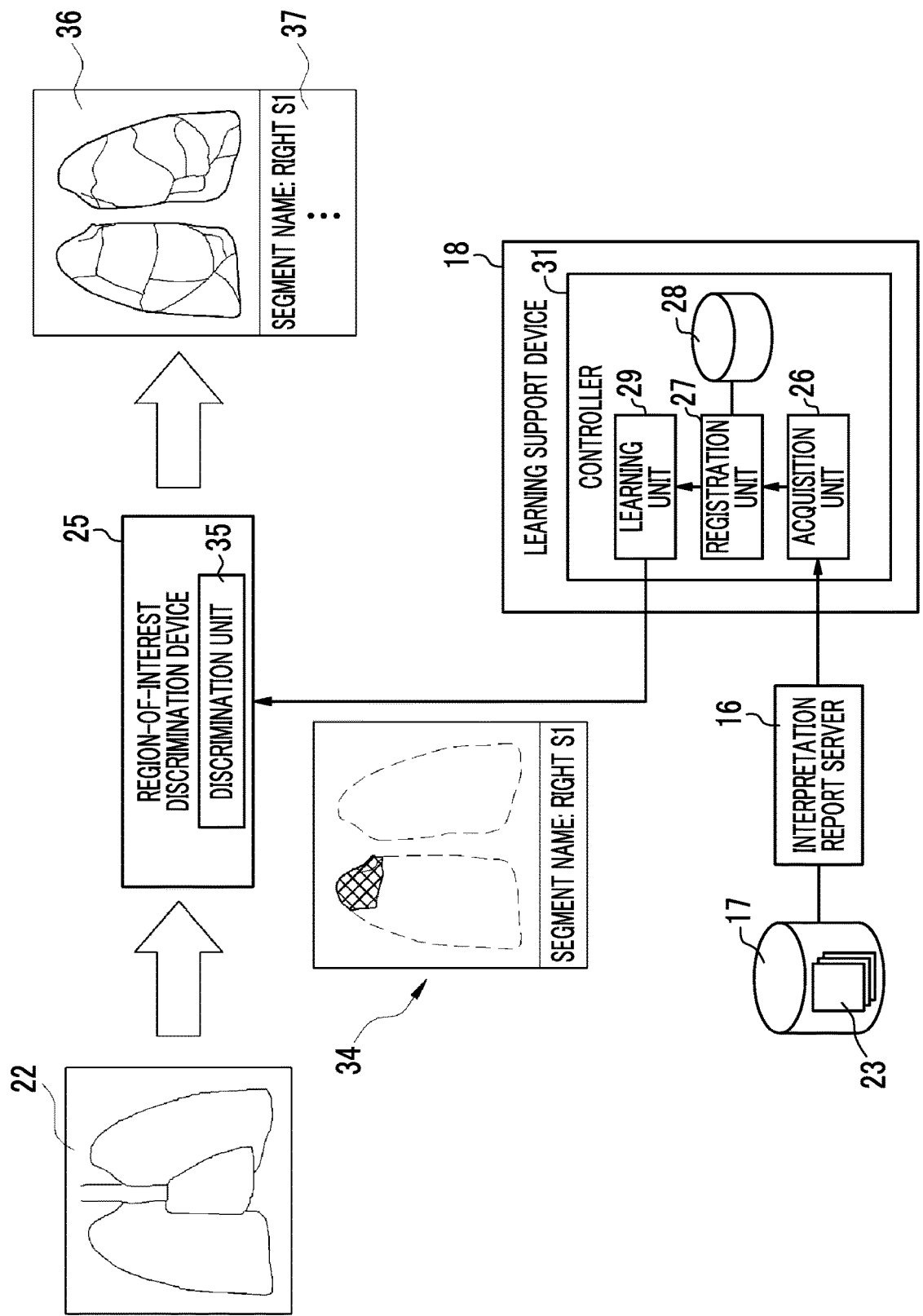
FIG. 2 is a diagram showing the schematic configuration of a learning support device of the invention.

FIG. 2 shows functional blocks of the learning support device 18 constituting the region-of-interest discrimination device 25. The region-of-interest discrimination device 25 of the invention is used along with the learning support device 18 connected to the network 21 and the interpretation report database 17 (see FIG. 1). The interpretation report database 17 functions as a storage unit of the invention.

The learning support device 18 is constituted of a general-purpose computer, and comprises a known hardware configuration including a CPU, a main storage device, such as a hard disc drive (HDD) or a solid state drive (SSD), an auxiliary storage device, an input/output interface, a communication interface, an input device, a display device, a data bus, and the like. A known operating system and the like are installed in the learning support device 18. The learning support device 18 performs transmission and reception of data to and from the image database 15 connected to the network 21 and the interpretation report database 17 through the communication interface.

In the embodiment, although the learning support device 18 is provided independently of the interpretation doctor terminal 12, the treatment department doctor terminal 13, the image management server 14, and the interpretation report server 16, the invention is not limited thereto, and the learning support device 18 may be provided in any one of the servers or the terminals.

As shown in FIG. 2, the learning support device 18 has an acquisition unit 26, a registration unit 27, a storage device 28, a learning unit 29, and a controller 31.

The acquisition unit 26 acquires an image of a region of interest included in the inspection image 22 of the interpretation report 23 and a name of the region of interest included in the text information of the interpretation report 23 by analyzing the interpretation report 23. In the embodiment, a name of a pulmonary segment is acquired as the name of the region of interest.

Figure 3:
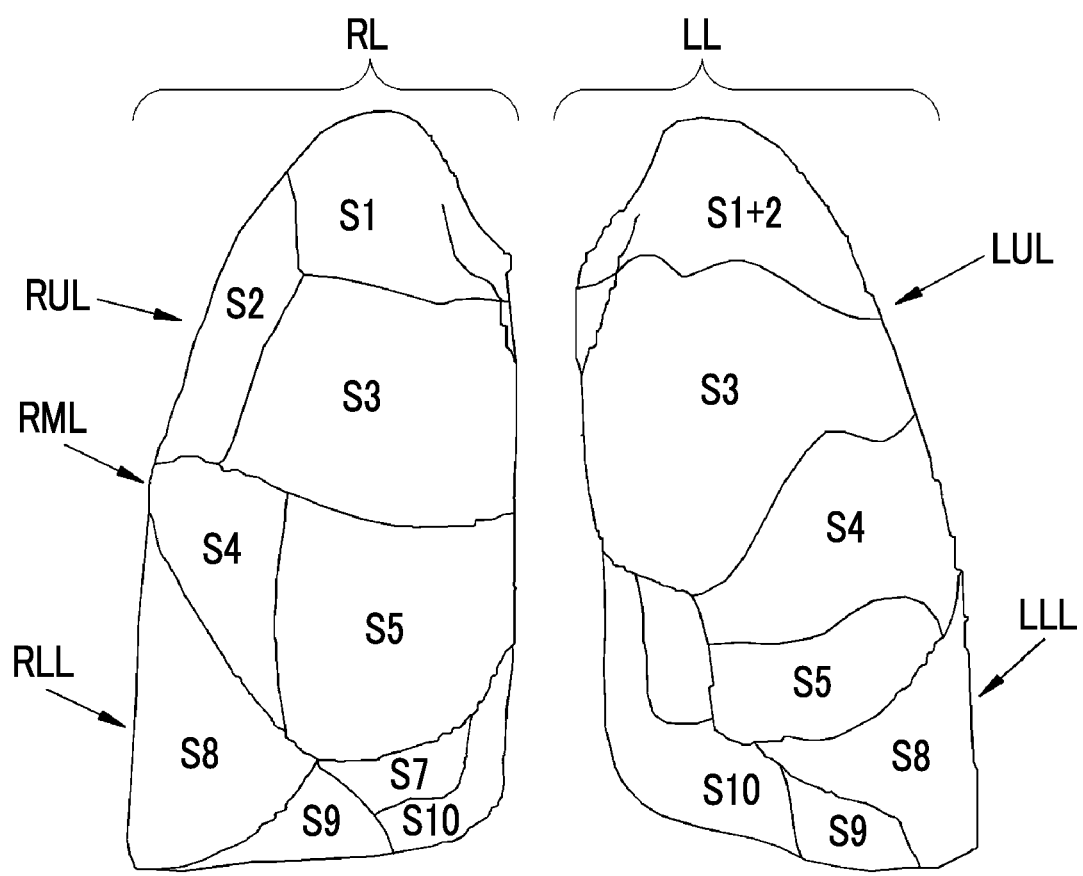
FIG. 3 is an explanatory view schematically showing each segment of a lung.

As shown in FIG. 3, a lung as an anatomical organ is divided into pulmonary lobes or pulmonary segments. A right lung RL is divided into a right upper lobe RUL, a right middle lobe RML, and a right lower lobe RLL as pulmonary lobes, and a left lung LL is divided into a left upper lobe LUL and a left lower lobe LLL as pulmonary lobes.

The right upper lobe RUL is divided into a right apical segment S1 (hereinafter, abbreviated as right S1: the following pulmonary segments are abbreviated in the same manner), a right posterior segment S2, and a right anterior segment S3 as pulmonary segments. The right middle lobe RML is divided into a right lateral segment S4 and a right medial segment S5 as pulmonary segments. The right lower lobe RLL is divided into a right superior segment S6, a right medial basal segment S7, a right anterior basal segment S8, a right lateral basal segment S9, and a right posterior basal segment S10 as pulmonary segments.

The left upper lobe LUL is divided into a left apicoposterior segment S1+2, a left anterior segment S3, a left superior lingular segment S4, and a left inferior lingular segment S5 as pulmonary segments. The left lower lobe LLL is divided into a left superior segment S6, a left anterior basal segment S8, a left lateral basal segment S9, and a left posterior basal segment S10 as pulmonary segments.

The controller 31 controls a flow of processing of the acquisition unit 26, the registration unit 27, and the learning unit 29. Processing in which the acquisition unit 26 acquires an image of a region of interest included in the inspection image 22 of the interpretation report 23 and a name of the region of interest included in the text information of the interpretation report 23 will be described referring to FIGS. 4 and 5.

In the interpretation report 23, the inspection image 22 to be a target to be interpreted, accessory information 23A, finding information 23B, and link information 23C are included. The accessory information 23A is text information attached to the inspection image 22 to be a target to be interpreted, such as the patient ID, the inspection ID, and the inspection date. The finding information 23B is obtained by editing a finding of the interpretation doctor who interprets the inspection image 22 to be a target to be interpreted, and is text information input from the interpretation doctor terminal 12. The link information 23C is used in displaying the interpretation report 23 on the display as described below, and is link information associating the finding information 23B with positional information of the region of interest included in the inspection image 22.

Figure 5:
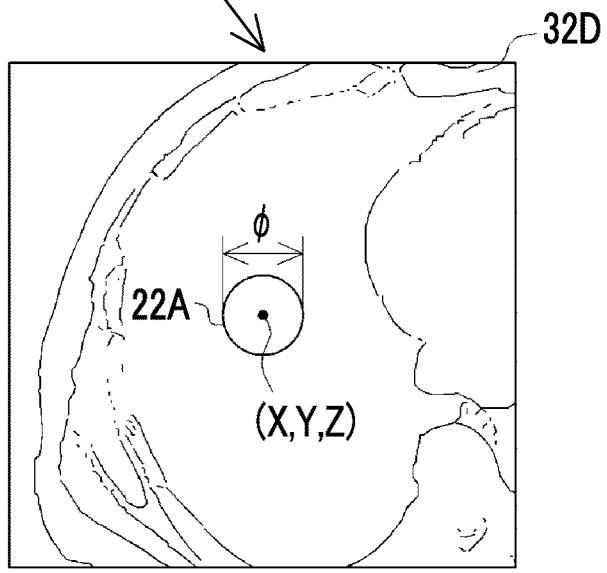
FIG. 5 is an explanatory view illustrating a method of acquiring a name of a region of interest and positional information of the region of interest from the interpretation report.

FIG. 5 shows an example of a display screen 32 in a case where the interpretation report 23 is displayed on the display of the interpretation doctor terminal 12 or the treatment department doctor terminal 13. In the example, an accessory information display field 32A in which the accessory information 23A is displayed, a finding field 32B in which the finding information 23B is displayed, and an image display field 32C in which a thumbnail image of the inspection image 22 to be a target to be interpreted is displayed are provided in order from the top.

In the example shown in FIG. 5, the finding information 23B "Boundary-clear pulmonary nodule having φ=30 mm is recognized in right S1." is displayed in the finding field 32B. In this case, "pulmonary nodule" indicating a lesion name of the region of interest, "right S1" indicating a pulmonary segment name of the region of interest, and "φ=30 mm" indicating a diameter of the region of interest are highlighted.

In the embodiment, the link information 23C is included in the interpretation report 23, and the link information 23C associates the words "pulmonary nodule" indicating the lesion name in the finding information 23B with the positional information of the region of interest included in the inspection image 22. The positional information of the region of interest is specifically the coordinates of the region of interest in the inspection image 22 and a range around the coordinates. As the link information 23C is provided, in a case where the interpretation doctor terminal 12 or the treatment department doctor terminal 13 is operated and "pulmonary nodule" highlighted in the display screen 32 is selected, an image 22A of the region of interest based on the associated positional information of the region of interest can be displayed on the display. In the example shown in FIG. 5, in a case where "pulmonary nodule" is selected, a range including region of interest (a portion surrounded by a circle) having a diameter of φ=30 mm around coordinates (X,Y,Z) in the inspection image 22 is cut, and an image 32D enlarged around the positional information of the region of interest included in the link information 23C is displayed.

Figure 4:
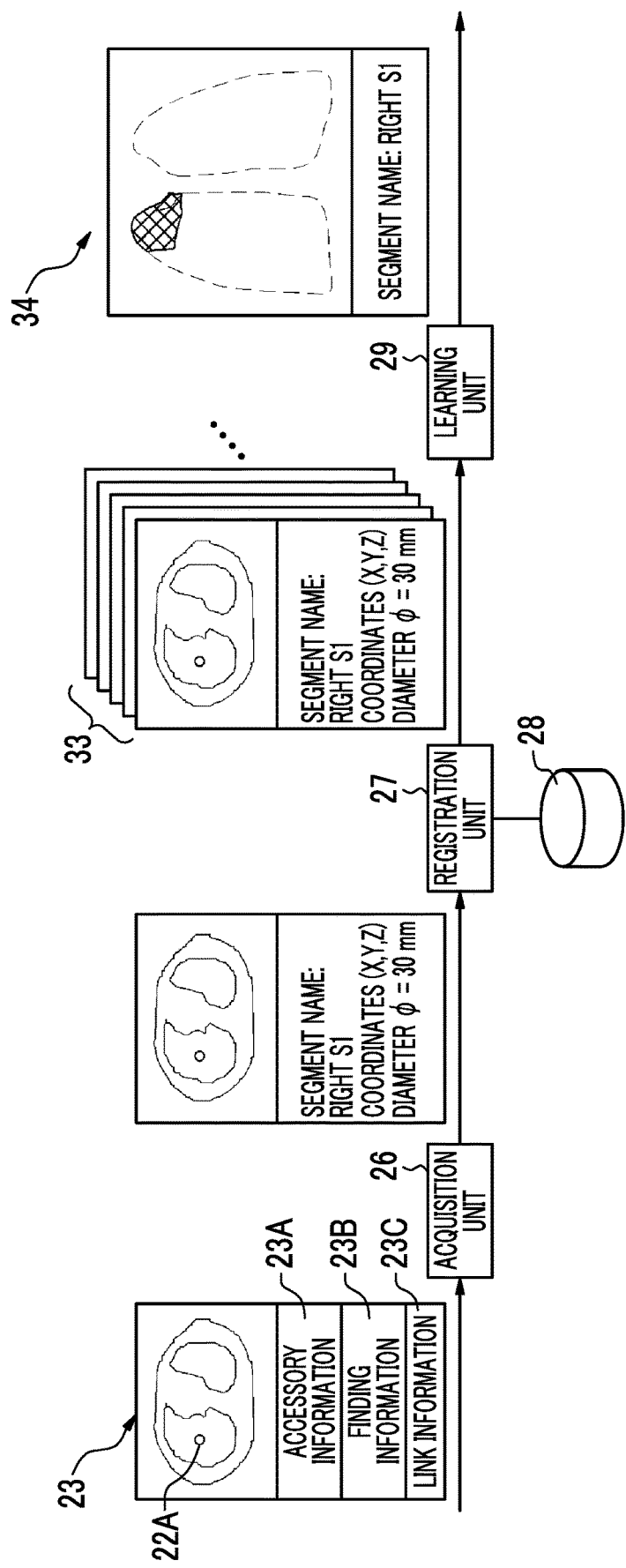
FIG. 4 is an explanatory view illustrating a method of acquiring training data from an interpretation report and generating discrimination model.

In the example shown in FIGS. 4 and 5, the acquisition unit 26 analyzes text of the finding information 23B of the interpretation report 23, acquires "right S1" indicating the name of the pulmonary segment as the name of the region of interest, and acquires positional information consisting of the coordinates (X,Y,Z) of the region of interest in the inspection image 22 from the link information 23C of the interpretation report 23 and "φ=30 mm" indicating the diameter of the region of interest.

The registration unit 27 registers training data 33 consisting of the image 22A of the region of interest and the name of the region of interest acquired by the acquisition unit 26 in the storage device 28. In the example shown in FIG. 4, training data 33 consisting of the image 22A of the region of interest, "right S1" indicating the name of the pulmonary segment, the coordinates (X,Y,Z) indicating the positional information, and the diameter φ=30 mm is registered. The storage device 28 may be, for example, a part of a storage device provided in the learning support device 18, such as a hard disc drive (HDD) or a solid state drive (SSD), or may be a storage device connected to the learning support device 18 through the network 21.

With the process described above, the registration unit 27 registers a plurality of pieces of training data 33, and, for example, until a predetermined number of pieces of training data 33 is registered in the storage device 28 or training data 33 based on all interpretation reports 23 registered in the interpretation report database 17 are registered in the storage device 28 for machine learning or the like described below, the acquisition of the image 22A of the region of interest and the name of the region of interest from the interpretation report 23 and the registration of the training data 33 are repeated.

The learning unit 29 performs learning for generating a discrimination model 34, which outputs the image 22A of the region of interest and the name of the region of interest with respect to an input of the inspection image 22 of the interpretation report 23, using a plurality of pieces of training data 33 registered in the storage device 28. Specifically, the discrimination model 34 is generated using a machine learning method, such as deep learning. For example, a plurality of pieces of training data 33 are input, and a machine learning algorithm is made to learn the relationship between the positional information of the region of interest and a feature quantity (pixel value or the like) of each voxel. Specifically, a weighting coefficient for learning to be used in the machine learning algorithm is updated such that an error between positional information obtained in a case where a feature quantity around the region of interest among the feature quantities of the respective voxels is input and the positional information of the region of interest in training data 33 is minimized.

As above, the discrimination model 34 generated by the learning unit 29 is transmitted to the region-of-interest discrimination device 25. In a discrimination unit 35 of the region-of-interest discrimination device 25, in a case where the inspection image 22 of the interpretation report 23 or the like is input, the image 22A of the region of interest and the name of the region of interest in the inspection image 22 are output using the discrimination model 34.

The discrimination model 34 includes the weighting coefficient decided using the above-described machine learning method, and in a case where the inspection image 22 is input, is used to discriminate the image 22A of the region of interest and the name of the region of interest.

The discrimination unit 35 discriminates the image of the region of interest in the inspection image and the name of the region of interest using the discrimination model 34. The discrimination unit 35 makes a display or the like of the region-of-interest discrimination device 25 display the discriminated image 36 of the region of interest, the discriminated name 37 of the region of interest, and the like.

Figure 6:
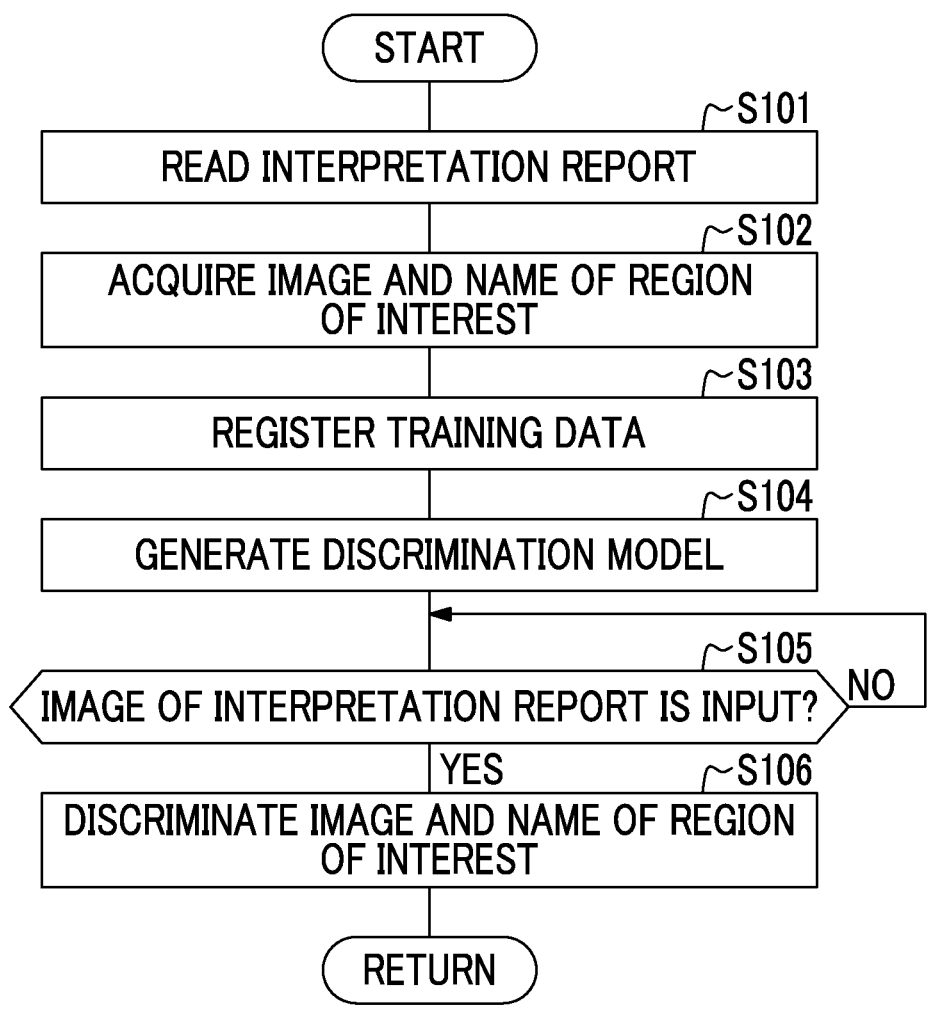
FIG. 6 is a flowchart illustrating the operation of the learning support device and the region-of-interest discrimination device of the invention.

Hereinafter, a process in which a discrimination model 34 is generated from an interpretation report 23 having an inspection image 22 of a lung, and an image of a region of interest and a name of the region of interest are discriminated will be described referring to a flowchart of FIG. 6.

In the learning support device 18, first, an interpretation report 23 relating to a pulmonary disease is read from the interpretation report database 17 (S101).

Next, the acquisition unit 26 acquires an image of a region of interest included in the inspection image 22 of the interpretation report 23 and a name of the region of interest included in the text information of the interpretation report 23 (S102), and the registration unit 27 registers training data 33 consisting of the image of the region of interest and the name of the region of interest acquired by the acquisition unit 26 in the storage device 28 (S103). As described above, in a case where the finding information 23B "Boundary-clear pulmonary nodule having φ=30 mm is recognized in right S1.", and the link information 23C are included in the interpretation report 23, "right S1" indicating the pulmonary segment name of the region of interest and positional information of the region of interest included in the link information 23C are acquired.

Then, in a case where training data 33 for machine learning or the like is registered in the storage device 28, the learning unit 29 performs learning for generating the discrimination model 34 using a plurality of pieces of registered training data 33 (S104). The generated discrimination model 34 is transmitted to the region-of-interest discrimination device 25.

In a case where a new inspection image 22 is input to the region-of-interest discrimination device 25 (in S105, YES), the discrimination unit 35 outputs the image of the region of interest in the inspection image 22 and the name of the region of interest using the discrimination model 34. For example, color-coding display of the pulmonary segment, name display of the pulmonary segment, or the like is performed (S106).

As above, since the learning support device 18 performs learning based on training data composed of the image of the region of interest and the name of the region of interest acquired from the interpretation report 23, in the medical information system, training data can be acquired from the interpretation reports used heretofore, and training data needed for learning can be easily acquired. In addition, since the discrimination model 34 can be generated using training data, and the discrimination model 34 is generated based on the interpretation report in which correct information is recorded, the accuracy of discrimination can be easily improved.

In the embodiment, although the region-of-interest discrimination device 25 that can output "right S1" as the region of interest has been exemplified, the invention is not limited thereto, and a discrimination model that can discriminate a plurality of regions of interest simultaneously, that is, can discriminate a plurality of regions of interest simultaneously in such a manner that a voxel in any range in the input inspection image is "right S1" and a voxel in another range is "right S2" may be created. Alternatively, the discrimination model may be applied to the region-of-interest discrimination device such that a plurality of regions of interest can be discriminated simultaneously.

Figure 7:
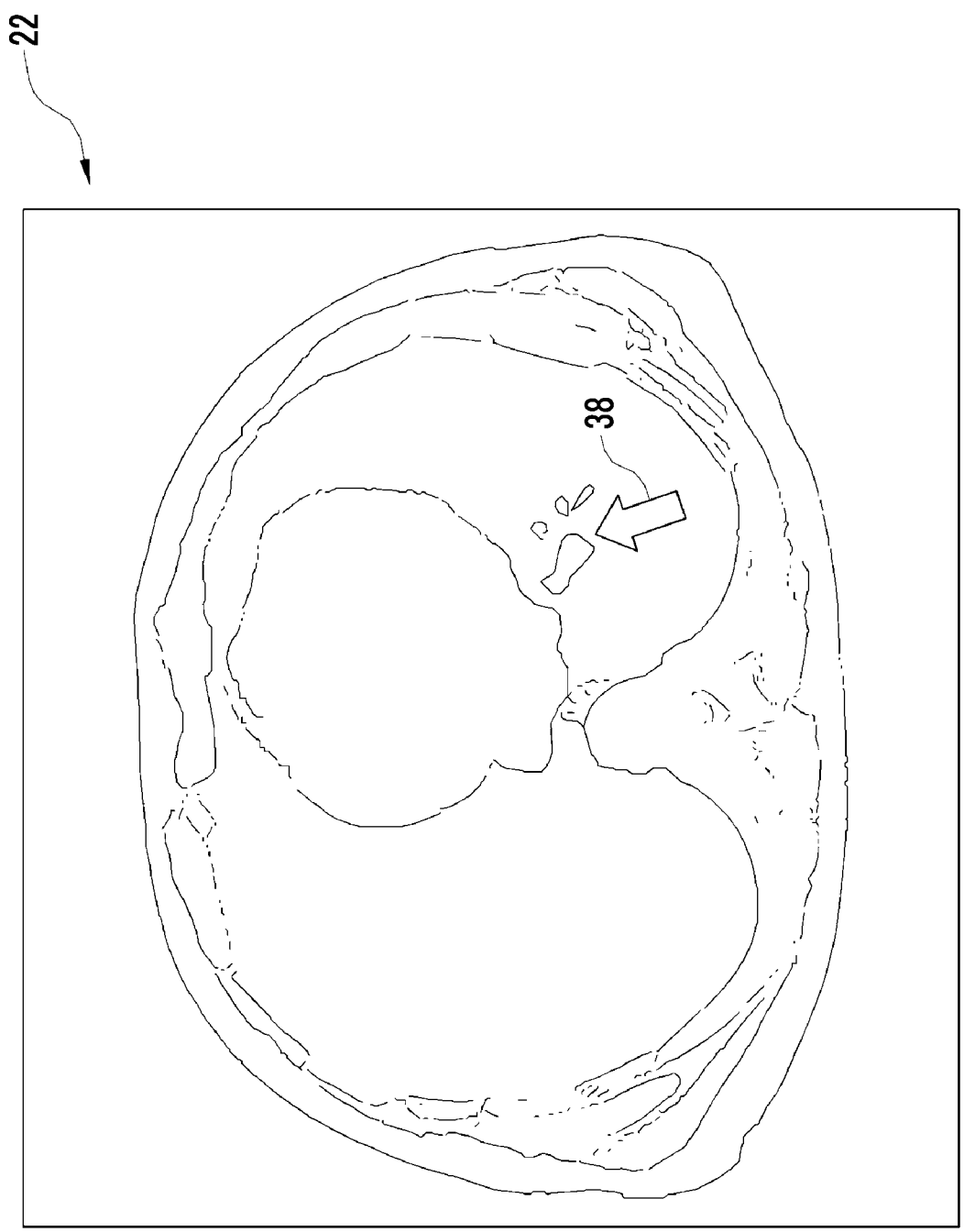
FIG. 7 is an explanatory view illustrating a modification example where the positional information of the region of interest is acquired from annotation information.

In the above-described embodiment, although an example where the positional information of the region of interest is acquired from the link information 23C included in the interpretation report 23 has been described, the invention is not limited thereto, and in a case where the interpretation report 23 has annotation information, the acquisition unit 26 may acquire positional information of a region of interest from the annotation information. The annotation information is information given to image data or the like as an annotation, and in an example shown in FIG. 7, an arrow 38 as annotation information is included in the inspection image 22, and the arrow 38 is attached around the region of interest. In this case, the acquisition unit 26 acquires, for example, the coordinates of a tip position of the arrow 38 in the inspection image 22 as positional information.

The acquisition unit 26 may comprise a region-of-interest discrimination unit, and may discriminate a region of interest from the inspection image 22 of the interpretation report 23 with the region-of-interest discrimination unit. In this case, the configuration of the region-of-interest discrimination unit is the same configuration as the region-of-interest discrimination device 25 of the above-described embodiment, that is, the configuration in which a region of interest is discriminated from the inspection image 22 of the interpretation report 23 using the learned and generated discrimination model 34 and is registered as new training data.

As another modification example, in a case where the acquisition unit 26 acquires names of a plurality of regions of interest including a first name and a second name different from the first name by analyzing the interpretation report 23, the learning unit 29 performs learning using first training data including the first name as the name of the region of interest and second training data including the second name as the name of the region of interest. In this case, for example, in a case where two names of "right S1" and "right S2" are acquired from the text information "Pulmonary nodule is recognized in right S1/right S2 . . . " in the interpretation report 23, the registration unit 27 registers training data 33 using the name "right S1" and training data 33 using the name "right S2", respectively.

The learning unit 29 updates the weighting coefficient for learning to be used in the machine learning algorithm such that both of an error of the positional information of the region of interest in a case where training data 33 using the name "right S1" is input and an error of the positional information of the region of interest in a case where training data 33 using the name "right S2" is input are minimized. With this, the accuracy of learning can be improved.

Figure 8:
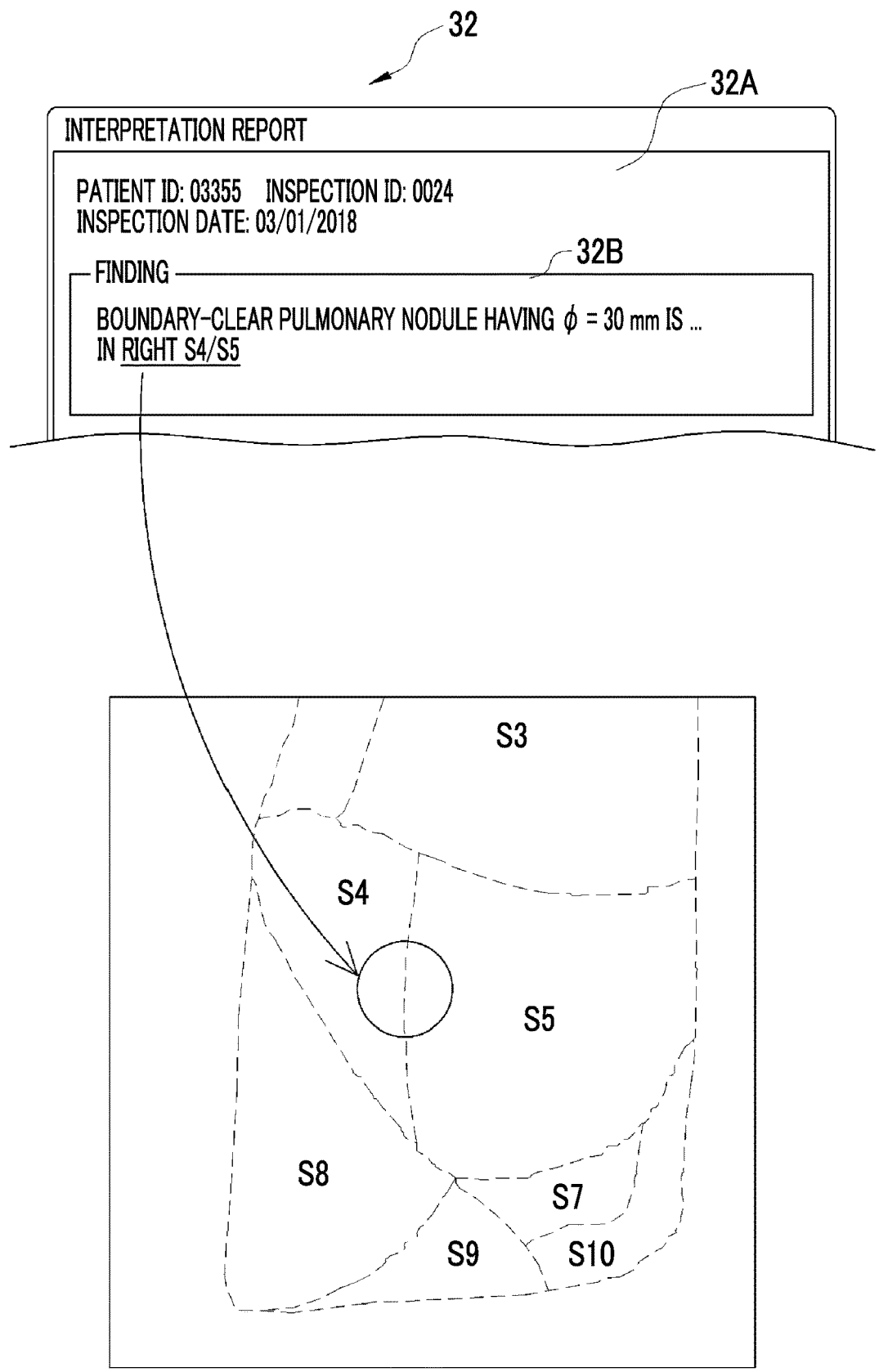
FIG. 8 is an explanatory view illustrating a modification example where the positional information of the region of interest is acquired using region position information.

In a case where the acquisition unit 26 acquires the names of a plurality of regions of interest by analyzing the interpretation report 23, the learning unit 29 may perform learning region position information relating to the positional information of the region of interest, in addition to training data 33. In this case, as shown in FIG. 8, the learning unit 29 stores in advance, as the region position information, for example, region position information that a right S4 is present on a side surface of the lung and a right S5 is present inside. Then, the acquisition unit 26 acquires two names of "right S4" and "right S5" by analyzing the interpretation report 23, the learning unit 29 makes a half of the region of interest in a direction of facies lateralis pulmonis be learned as "right S4" and makes a half of the region of interest in a direction of facies medialis pulmonis be learned as "S5" using the region position information.

The acquisition unit 26 may acquire a name of a superordinate concept or a subordinate concept with reference to a hierarchical structure database, and the learning unit 29 may perform learning using training data 33 consisting of the image of the region of interest and the name of the superordinate concept or the subordinate concept. The hierarchical structure database may be, for example, a database constructed using a part of the storage device provided in the learning support device 18 or may be a database connected to the learning support device 18 through the network 21. The hierarchical structure database stores the name of the superordinate concept or the subordinate concept corresponding to a superordinate concept or a subordinate concept with respect to the name of the region of interest. For example, in regard to the lung, the division of the pulmonary lobes and the pulmonary segments, and the like are stored in the hierarchical structure database, and a hierarchical structure of right lung>right upper lobe>right S1 in order from the superordinate concept to the subordinate concept is stored.

In this case, for example, in a case where the acquisition unit 26 acquires the name "right S1", the learning unit 29 acquires "right upper lobe" and "right lung" as the name of the superordinate concept with reference to the hierarchical structure database, and performs the same learning as in the above-described embodiment on the names "right upper lobe" and "right lung" in addition to "right S1" as training data 33.

Figure 9:
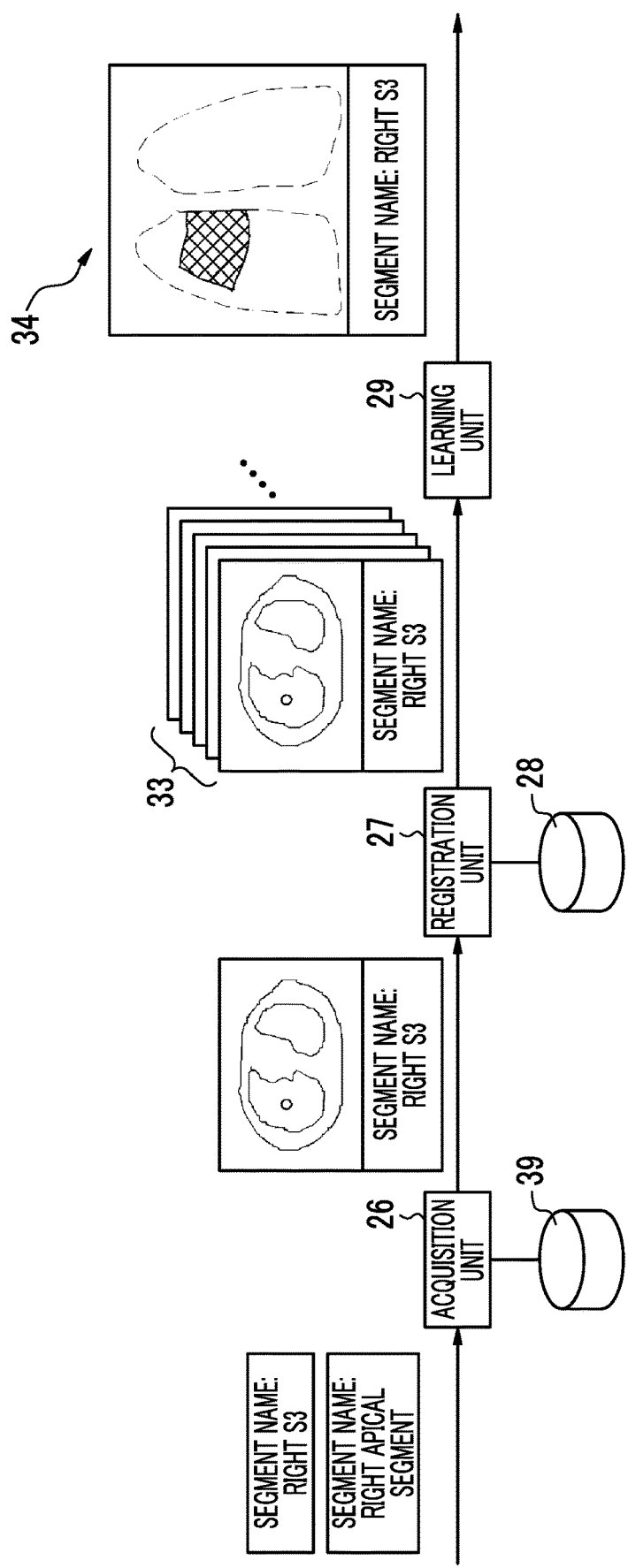
FIG. 9 is an explanatory view illustrating a modification example where the positional information of the region of interest is acquired with reference to a similar name database.

The acquisition unit 26 may decide a representative name from a plurality of similar names with reference to a similar name database 39, and the learning unit 29 may perform learning using training data 33 consisting of the image of the region of interest and the representative name. As shown in FIG. 9, the similar name database 39 may be, for example, a database constructed using a part of the storage device provided in the learning support device 18 or may be a database connected to the learning support device 18 through the network 21. The similar name database 39 is a database that stores a plurality of similar names similar to one another with respect to the name of the region of interest in advance, and stores a plurality of similar names, such as segment names; "right S3" and "right apical segment". In the example, the acquisition unit 26 decides "right S3" as the representative name, and the learning unit 29 performs the same learning as in the above-described embodiment using training data 33 consisting of the image of the region of interest and "right S3" as the name.

It is preferable that the acquisition unit 26 newly acquires the image of the region of interest and the name of the region of interest in a case where the interpretation report 23 is newly stored in the interpretation report database 17, the registration unit 27 registers new training data 33 consisting of the image of the region of interest and the name of the region of interest newly acquired by the acquisition unit 26, and the learning unit 29 generates an updated discrimination model 34 by performing learning again using a plurality of pieces of training data including new training data 33 in a case where new training data 33 is registered. With this, the discrimination accuracy of the discrimination model 34 can be improved.

In the above-described embodiment, although the interpretation report 23 created by the interpretation doctor with the interpretation doctor terminal 12 or the like has been exemplified, an electronic medical chart including the same image and text information as the interpretation report 23 of the above-described embodiment may be applied.

Figure 10:
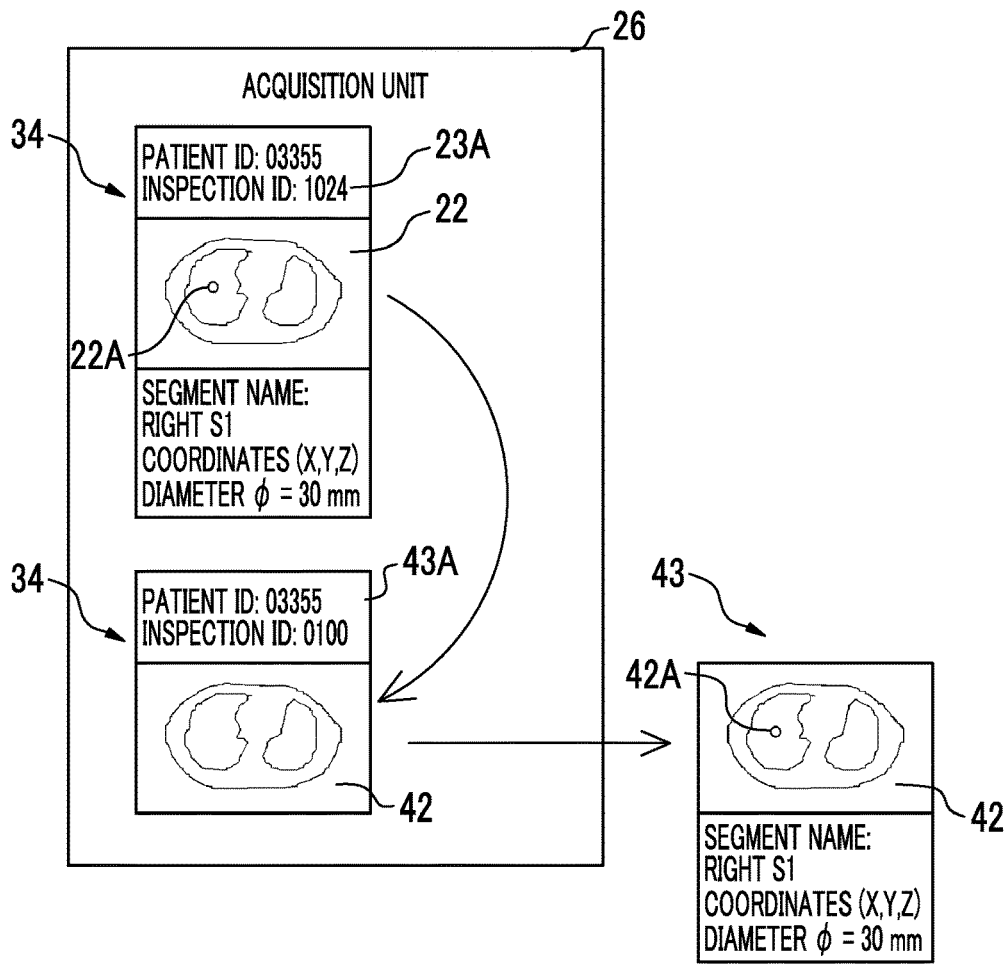
FIG. 10 is an explanatory view illustrating a modification example where the positional information of the region of interest is acquired from a past interpretation report.

In the above-described embodiment, although information on the region of interest is acquired from the interpretation report and is registered as training data, the invention is not limited thereto, and in a case where a past interpretation report not including information on the region of interest is stored, training data may be registered using the past interpretation report and a newly stored interpretation report. In this case, as shown in FIG. 10, in a case where a newly stored interpretation report 23 and a past interpretation report 43 for the same patient are stored in the interpretation report database 17, the acquisition unit 26 acquires an image 42A of the region of interest included in the inspection image 42 of the past interpretation report 43 by performing registration of an inspection image 42 of the past interpretation report 43, an inspection image 22 of the newly stored interpretation report 23, and a newly acquired image 22A of the region of interest through image processing or the like. In this case, the acquisition unit 26 determines that the interpretation reports 23 and 43 are for the same patient, for example, from the patient IDs included in the accessory information 23A and 43A.

The registration unit 27 registers past image training data 44 consisting of the image 42A of the region of interest acquired based on the past interpretation report 43 and a newly acquired name of the region of interest, and the learning unit 29 generates an updated discrimination model 34 by performing learning again using a plurality of pieces of training data 33 including past image training data 44 in a case where past image training data 44 is registered. With this, since the number of pieces of training data can be further increased, the discrimination accuracy of the discrimination model 34 can be improved.

Figure 11:
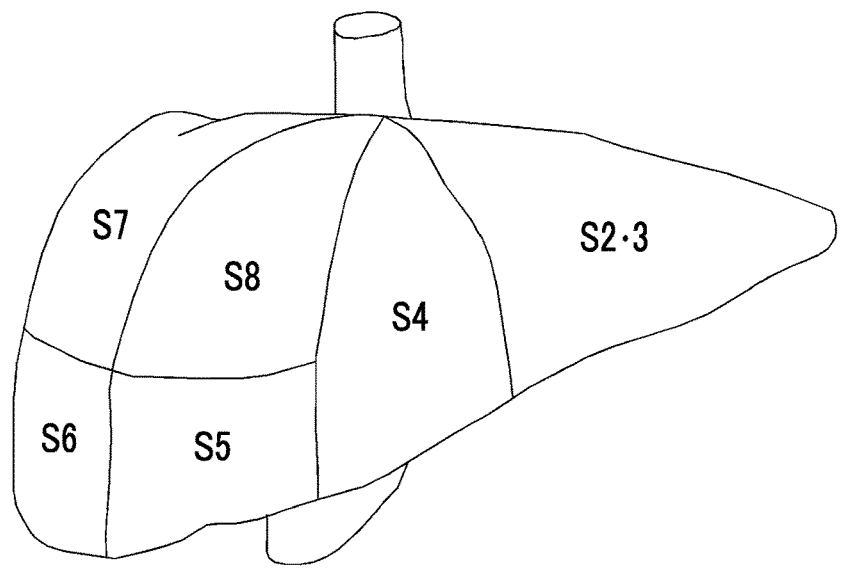
FIG. 11 is an explanatory view schematically showing each segment of a liver.

Although the acquisition unit 26 exemplifies the anatomical organ name as the name of the region of interest and the lung as the segment name, the invention is not limited thereto, and as shown in FIG. 11, each segment (caudate lobe S1, left lobes S2, S3, and S4, right lobes S5, S6, and S7, and the like) or each segment of a brain may be applied. Alternatively, the acquisition unit 26 may acquire a disease name and a symptom as the region of interest.

In the above-described embodiment, although the learning support device 18 is provided separately from the region-of-interest discrimination device 25, the learning support device 18 may be integrated into the region-of-interest discrimination device 25.

In the above-described respective embodiments, as the hardware structures of processing units that execute various kinds of processing, such as the acquisition unit 26, the registration unit 27, the learning unit 29, and the discrimination unit 35, for example, a CPU that is a general-purpose processor functioning as various processing units by executing a software program as described above is exemplified. Various processors may be used instead of all or a part of the functions that are implemented by the CPU. The hardware structure of various processors is, more specifically, an electric circuit (circuitry), in which circuit elements, such as semiconductor elements, are combined. The hardware structure of a storage unit is a storage device, such as a hard disc drive (HDD) or a solid state drive (SSD).

Various embodiments or various modification examples described above may be combined as appropriate. The invention also extends to a storage medium storing the program, in addition to the program.

Note that the invention can be applied to a field other than a medical field using an interpretation report. Specific information including text information and image information may be used, and for example, the invention may be applied to a field using a photographic image (image data) including text information or a field using social networking service (SNS) information.

[Supplementary Item 1]

A learning support device comprising:

a storage unit that stores specific information including an image and text information;

an acquisition unit that acquires an image of a region of interest included in the image and a name of the region of interest included in the text information by analyzing the text information;

a registration unit that registers training data consisting of the image of the region of interest and the name of the region of interest acquired by the acquisition unit; and a learning unit that performs learning for generating a discrimination model, which outputs the image of the region of interest and the name of the region of interest with respect to an input of the image of the specific information, using the training data registered in the registration unit.

[Supplementary Item 2]

The specific information includes text information in a photographic image.

[Supplementary Item 3]

The specific information is SNS information.

EXPLANATION OF REFERENCES

2: medical information system
11: modality
11A: CT apparatus
11B: MRI apparatus
11C: CR apparatus 12: interpretation doctor terminal
13: treatment department doctor terminal
14: image management server
15: image database
16: interpretation report server
17: interpretation report database
18: learning support device
19: order management server
21: network
22: inspection image
22A: image
23: interpretation report
23A: accessory information
23B: finding information
23C: link information
25: region-of-interest discrimination device
26: acquisition unit
27: registration unit
28: storage device
29: learning unit
31: controller
32: display screen
32A: accessory information display field
32B: finding field
32C: image display field
32D: image
33: training data
34: discrimination model
35: discrimination unit
36: image
37: name
38: arrow
39: similar name database
42: inspection image
42A: image
43: interpretation report
43A: accessory information
44: past image training data

What is claimed is:

1. A learning support device comprising:
a database, configured to store an interpretation report including an image and text information; and
a processor, connected to the database and configured to:
acquire an image of a region of interest included in the image and a name of the region of interest included in the text information by analyzing the interpretation report;
register training data consisting of the image of the region of interest and the name of the region of interest; and
perform learning for generating a discrimination model, which outputs the image of the region of interest and the name of the region of interest with respect to an input of the image of the interpretation report, using a plurality of pieces of the training data.

2. The learning support device according to claim 1,
wherein the processor acquires positional information of the region of interest by analyzing the interpretation report.

3. The learning support device according to claim 2,
wherein the interpretation report has link information for associating finding information included in the text information with the positional information of the region of interest included in the image, and
the processor acquires the positional information of the region of interest from the link information.

4. The learning support device according to claim 2,
wherein the interpretation report has annotation information attached around the region of interest, and
the processor acquires the positional information of the region of interest from the annotation information.

5. The learning support device according to claim 2,
the processor further configured to discriminate the region of interest from the image of the interpretation report, and
wherein the processor acquires the image of the region of interest and the positional information of the region of interest.

6. The learning support device according to claim 1,
wherein, in a case where names of a plurality of regions of interest including a first name and a second name different from the first name are acquired by analyzing the interpretation report, the processor performs the learning using first training data including the first name as the name of the region of interest and second training data including the second name as the name of the region of interest.

7. The learning support device according to claim 2,
wherein, in a case where names of a plurality of regions of interest including a first name and a second name different from the first name are acquired by analyzing the interpretation report, the processor performs the learning using first training data including the first name as the name of the region of interest and second training data including the second name as the name of the region of interest.

8. The learning support device according to claim 2,
wherein, in a case where names of a plurality of regions of interest are acquired by analyzing the interpretation report, the processor performs learning using region position information relating to the positional information of the region of interest in addition to the training data.

9. The learning support device according to claim 1,
wherein the processor acquires, with reference to a hierarchical structure database that stores a name in a superordinate concept or a subordinate concept corresponding to a superordinate concept or a subordinate concept with respect to the name of the region of interest, the name in the superordinate concept or the subordinate concept from the name of the region of interest, and
the processor performs the learning using training data consisting of the image of the region of interest and the name in the superordinate concept or the subordinate concept.

10. The learning support device according to claim 1,
wherein the processor decides, with reference to a similar name database that stores a plurality of similar names similar to one another in advance with respect to the name of the region of interest, a representative name from the plurality of similar names, and
the processor performs the learning using training data consisting of the image of the region of interest and the representative name.

11. The learning support device according to claim 1,
wherein the processor newly acquires an image of the region of interest and a name of the region of interest in a case where the interpretation report is newly stored in the database,
the processor registers new training data consisting of the image of the region of interest and the name of the region of interest newly acquired by the processor, and the processor generates an updated discrimination model by performing learning again using a plurality of pieces of the training data including the new training data in a case where the new training data is registered.

12. The learning support device according to claim 11, wherein, in a case where the newly stored interpretation report and a past interpretation report for the same patient are stored in the database, the processor acquires an image of the region of interest included in an image of the past interpretation report by performing registration of the image of the past interpretation report, an image of the newly stored interpretation report, and the newly acquired image of the region of interest, the processor registers past image training data consisting of the image of the region of interest acquired based on the past interpretation report and the newly acquired name of the region of interest, and the processor generates the updated discrimination model by performing learning again using a plurality of pieces of the training data including the past image training data in a case where the past image training data is registered.

13. The learning support device according to claim 1, wherein the interpretation report includes an electronic medical chart.

14. The learning support device according to claim 1, wherein the processor acquires, as the name of the region of interest, an anatomical organ name, a segment name, a disease name, and a symptom.

15. A learning support method for a learning support device including a database configured to store an interpretation report including an image and text information, and a processor connected to the database, the learning support method comprising:
    an acquisition step in which the processor acquires an image of a region of interest included in the image and a name of the region of interest included in the text information by analyzing the interpretation report;
    a registration step in which the processor registers training data consisting of the image of the region of interest and the name of the region of interest; and
    a learning step in which the processor performs learning for generating a discrimination model, which outputs the image of the region of interest and the name of the region of interest with respect to an input of the image of the interpretation report, using a plurality of pieces of the training data.

16. A non-transitory computer readable recording medium storing a learning support program that causes a computer to function as:
    storing an interpretation report including an image and text information;
    acquiring an image of a region of interest included in the image and a name of the region of interest included in the text information by analyzing the interpretation report;
    registering training data consisting of the image of the region of interest and the name of the region of interest; and
    performing learning for generating a discrimination model, which outputs the image of the region of interest and the name of the region of interest with respect to an input of the image of the interpretation report, using a plurality of pieces of the training data.

17. A region-of-interest discrimination device comprising:
    a database, configured to store an interpretation report including an image and text information; and
    a processor, connected to the database and configured to:
    acquire an image of a region of interest included in the image and a name of the region of interest included in the text information by analyzing the interpretation report;
    register training data consisting of the image of the region of interest and the name of the region of interest;
    perform learning for generating a discrimination model, which outputs the image of the region of interest and the name of the region of interest with respect to an input of the image of the interpretation report, using a plurality of pieces of the training data; and
    discriminate the image of the region of interest and the name of the region of interest using the discrimination model in a case where the image of the interpretation report is input.

18. A region-of-interest discrimination method for a region-of-interest discrimination device including a database configured to store an interpretation report including an image and text information, and a processor connected to the database, the region-of-interest discrimination method comprising:
    an acquisition step in which the processor acquires an image of a region of interest included in the image and a name of the region of interest included in the text information by analyzing the interpretation report;
    a registration step in which the processor registers training data consisting of the image of the region of interest and the name of the region of interest;
    a learning step in which the processor performs learning for generating a discrimination model, which outputs the image of the region of interest and the name of the region of interest with respect to an input of the image of the interpretation report, using a plurality of pieces of the training data; and
    a discrimination step in which the processor discriminates the image of the region of interest and the name of the region of interest using the discrimination model in a case where the image of the interpretation report is input.

19. A non-transitory computer readable recording medium storing a region-of-interest discrimination program that causes a computer to function as:
    storing an interpretation report including an image and text information;
    acquiring an image of a region of interest included in the image and a name of the region of interest included in the text information by analyzing the interpretation report;
    registering training data consisting of the image of the region of interest and the name of the region of interest;
    performing learning for generating a discrimination model, which outputs the image of the region of interest and the name of the region of interest with respect to an input of the image of the interpretation report, using a plurality of pieces of the training data; and
    discriminating the image of the region of interest and the name of the region of interest using the discrimination model in a case where the image of the interpretation report is input.

* * * * *